United States Patent [19]

Brown et al.

[11] 4,299,832
[45] Nov. 10, 1981

[54] SUBSTITUTED THEOPHYLLINE COMPOUNDS

[75] Inventors: Roger C. Brown, Loughborough; Rodney A. Brown, East Leake; Stephen E. O'Connor, Long Whatton, all of England

[73] Assignee: Fisons Limited, London, England

[21] Appl. No.: 89,286

[22] Filed: Oct. 30, 1979

[30] Foreign Application Priority Data

Nov. 11, 1978 [GB] United Kingdom ............ 44168/78
Mar. 1, 1979 [GB] United Kingdom ............ 7353/79

[51] Int. Cl.³ .......................................... C07D 473/08
[52] U.S. Cl. .................................. 424/253; 544/267
[58] Field of Search ....................... 544/267; 424/253

[56] References Cited

U.S. PATENT DOCUMENTS 3,317,533 5/1967 DeRidder et al. ............... 544/267
3,632,742 1/1972 Eckert ........................... 544/267

Primary Examiner—Nicholas S. Rizzo
Attorney, Agent, or Firm—Merriam, Marshall & Bicknell

[57] ABSTRACT

The substituted theophyllines of the formula:

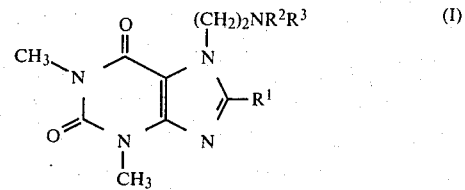

(wherein $R^1$, $R^2$ and $R^3$, which may be the same or different, each represent alkyl of 1 to 6 carbon atoms, cycloalkyl of 3 to 7 carbon atoms, phenyl or phenylalkyl of 7 to 10 carbon atoms, each of which may be unsubstituted or substituted by one or more hydroxy groups, alkoxy or alkylthio groups of 1 to 4 carbon atoms, halogen atoms, cyano groups, nitro groups, carboxy groups, alkoxycarbonyl groups of 2 to 5 carbon atoms, amino groups, alkylamino groups of 1 to 4 carbon atoms or dialkylamino groups of 2 to 8 carbon atoms, or when the group is phenyl or phenylalkyl, by one or more alkyl groups of 1 to 4 carbon atoms;

or $R^2$ and $R^3$ together represent a hydrocarbon chain of 3 to 6 carbon atoms optionally interrupted by a heteroatom;

and n represents an integer of from 1 to 6)
and the acid additional salts thereof, are novel compounds which are useful in the treatment of cardiac disorders. Processes for their preparation and pharmaceutical compositions containing them are also described.

8 Claims, No Drawings

SUBSTITUTED THEOPHYLLINE COMPOUNDS

This invention concerns certain substituted theophyllines, processes for their preparation, and pharmaceutical compositions containing them.

In one aspect, this invention provides the substituted theophyllines of the formula:

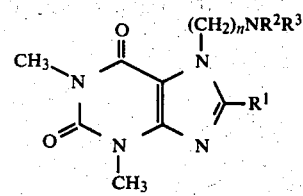

(wherein $R^1$, $R^2$ and $R^3$, which may be the same or different, each represent alkyl of 1 to 6 carbon atoms, cycloalkyl of 3 to 7 carbon atoms, phenyl or phenylalkyl of 7 to 10 carbon atoms, each of which may be unsubstituted or substituted by one or more hydroxy groups, alkoxy or alkylthio groups of 1 to 4 carbon atoms, halogen atoms, cyano groups, nitro groups, carboxy groups, alkoxycarbonyl groups of 2 to 5 carbon atoms, amino groups, alkylamino groups of 1 to 4 carbon atoms or dialkylamino groups of 2 to 8 carbon atoms, or, when the group is phenyl or phenylalkyl, by one or more alkyl groups of 1 to 4 carbon atoms;

or $R^2$ and $R^3$ together represents a hydrocarbon chain of 3 to 6 carbon atoms optionally interrupted by a heteroatom;

and n represents an integer of from 1 to 6)
and the acid addition salts thereof.

$R^1$, $R^2$ and $R^3$ each independently preferably represent alkyl of 1 to 4 carbon atoms which may be straight or branched, e.g. methyl, ethyl, n-propyl, isopropyl, n-butyl, isobutyl or t-butyl, and is desirably unsubstituted. $R^1$ most preferably represents methyl or ethyl.

When however one or more of $R^1$, $R^2$ and $R^3$ represents cycloalkyl, it is preferably of 5 or 6 carbon atoms, i.e. cyclopentyl or cyclohexyl, and is desirably unsubstituted.

When one or more of $R^1$, $R^2$ and $R^3$ represents phenylalkyl, it is preferably benzyl, 1-phenylethyl or 2-phenylethyl, and is desirably unsubstituted.

When one or more of $R^1$, $R^2$ and $R^3$ is substituted, however, it is desirably substituted by one or more hydroxy, methoxy, ethoxy, methylthio, ethylthio, cyano, nitro, carboxy, methoxycarbonyl, ethoxycarbonyl, amino, methylamino or dimethylamino groups, or by one or more fluorine, chlorine or bromine atoms, or, when the group is phenyl or phenylalkyl, by one or more methyl or ethyl groups. Specific preferred substituted groups which $R^1$, $R^2$ and/or $R^3$ may represent include 2-hydroxyethyl, 3-hydroxypropyl, 2-ethoxyethyl, 2-ethylthioethyl, trifluoromethyl, 4-methoxyphenyl, 4-chlorophenyl, 4-fluorophenyl, 4-cyanophenyl, 4-dimethylaminophenyl, 4-methylphenyl, 4-nitrophenyl, 4-methoxycarbonylphenyl and 3,5-dinitrophenyl.

When $R^2$ and $R^3$ represent separate groups, they are preferably identical.

When $R^2$ and $R^3$ together represent a hydrocarbon chain, it is preferably tetramethylene or pentamethylene. When such a hydrocarbon chain is interrupted by one or more heteroatoms, it is preferably interrupted by a single nitrogen (which may itself be alkylated, e.g. by methyl or ethyl, or arylated, e.g. by phenyl or benzyl) or oxygen atom.

The integer which n represents is preferably 1, 2, 3 or 4, more preferably 2, 3 or 4.

In a preferred group of compounds of formula I, $R^1$ represents unsubstituted alkyl of 1 to 4 carbon atoms (e.g. methyl or ethyl), $R^2$ and $R^3$ are identical and each represents unsubstituted alkyl of 1 to 4 carbon atoms (e.g. methyl, ethyl, n-propyl, isopropyl or n-butyl) and n represents 2, 3 or 4.

The acid addition salts of the compounds of formula I are preferably those formed with a pharmaceutically-acceptable mineral or organic acid, for example hydriodic, hydrochloric or hydrobromic acid, sulphuric acid, nitric acid, citric acid, tartaric acid or p-toluenesulphonic acid.

Specific preferred compounds of formula I are those of the Examples provided hereinafter and the acid addition salts thereof. Particular mention may be made however of 7-(2-N,N-diethylaminoethyl)-8-methyltheophylline and 7-(2-N,N-diethylaminoethyl)-8-ethyltheophylline and the acid addition salts thereof.

In another aspect, this invention provides a process for the preparation of a substituted theophylline of formula I, in which process a 7-unsubstituted theophylline of the formula:

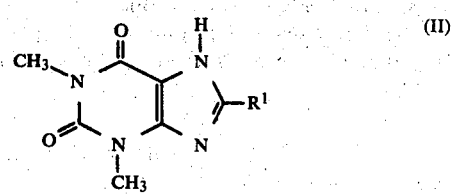

(wherein $R^1$ is as defined hereinbefore) is reacted in the presence of a base with a compound of the formula $R^2R^3N(CH_2)_nX$ (where $R^2$, $R^3$ and n are as defined hereinbefore, and X represents an anion-forming group) to give the desired compound.

Alternatively, the compounds of formula I may be prepared by reaction of a corresponding substituted theophylline of the formula:

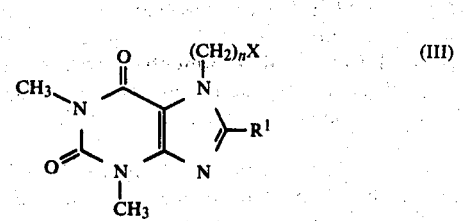

(wherein $R^1$, X and n are as defined hereinbefore) is reacted in the presence of a base with an amine of the formula $R^2R^3NH$, where $R^2$ and $R^3$ are as defined hereinbefore.

In the above processes, X preferably represents a halogen, e.g. chlorine, bromine or iodine, but may alternatively represent, for example, an arylsulphonyl e.g. benzenesulphonyl or toluenesulphonyl, or an alkanesulphonyl (e.g. methanesulphonyl) group, or a trialkyl ammonium (e.g. trimethylammonium) group.

The base employed in the above processes is preferably an alkali-metal base, e.g. sodium or potassium hydride or hydroxide.

The above processes are conveniently effected in an appropriate polar solvent, for example water, an alkanol (e.g. methanol or ethanol), or a dialkylformamide (e.g. dimethylformamide), or a mixture thereof.

The substituted theophyllines of formula III, which are themselves novel compounds, may be prepared by reacting a compound of formula II as defined hereinbefore with an α,ω-dihaloalkane of 1 to 6 carbon atoms in the presence of a base.

The α,ω-haloalkane employed is preferably a dibromoalkane, e.g. 1,2-dibromethane, and the base is preferably an alkali-metal base, e.g. sodium or potassium hydroxide.

The compounds of formula I may alternatively be prepared by techniques known per se from the analogous 7-(ω-aminoalkyl) compounds of formula I wherein at least one of $R^2$ and $R^3$ represents hydrogen, by one or more substitution reactions with suitable alkylating, arylating or aralkylating agents.

The 7-unsubstituted theophyllines of formula II may themselves be prepared by a process in which 1,3-dimethyl-4,5-diaminopyrimidine-2,6-dione is reacted with an acid halide of formula $R^1COHal$ then with a base, or is reacted with an acid anhydride of formula $(R^1CO)_2O$ to give the desired compound, or is reacted with an aldehyde of formula $R^1CHO$ to give an imine which is subsequently cyclised, e.g. by means of a Lewis acid (e.g. mercuric chloride) or thionyl chloride.

Hal preferably represents chlorine.

The compounds of formula I may alternatively be prepared by a process in which a compound of the formula:

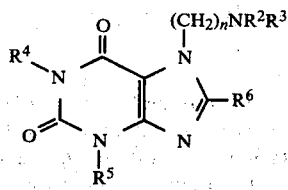

(wherein $R^2$, $R^3$ and n are as defined hereinbefore, $R^4$ and $R^5$ each represent hydrogen or methyl, and $R^6$ represents hydrogen or a group $R^1$ as defined hereinbefore, provided that $R^6$ represents methyl or at least one of $R^4$, $R^5$ and $R^6$ represents hydrogen) is methylated (when $R^4$ and/or $R^5$ represents hydrogen) or appropriately alkylated, arylated or aralkylated (when $R^6$ represents hydrogen or methyl to give the desired compound.

The alkylation, arylation or aralkylation may conveniently be effected by means of a suitable alkylating, arylating or aralkylating agent in the presence of a base (e.g. n-butyl lithium by conventional techniques.

The compounds of formula I may alternatively be prepared by a process in which a compound of the formula:

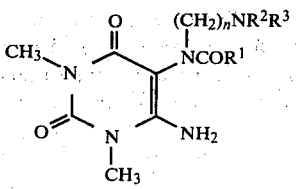

(wherein $R^1$, $R^2$, $R^3$ and n are as defined hereinbefore) is dehydrated and cyclised by means of a suitable dehydrating agent.

The dehydrating agent employed may be any suitable dehydrating agent which does not affect the remainder of the molecule, for example a thionyl halide, e.g. thionyl chloride.

The compounds of formula V may themselves be prepared by acylation of the corresponding compounds of the formula:

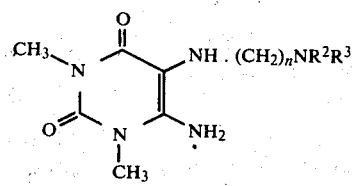

(wherein $R^2$, $R^3$ and n are as defined hereinbefore).

The acylation techniques employed may be those conventionally used in the art, for example reaction with an appropriate acylating agent, e.g. the appropriate acyl halide.

In turn, the compounds of formula VI may be prepared from the diaminouracil of the formula:

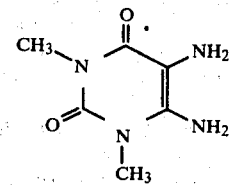

by a two-step synthesis in which the diaminouracil is first reacted with a compound of the formula $R^3R^2N(CH_2)_{n-1}CHO$ (wherein $R^2$, $R^3$ and n are as defined hereinbefore) to give a compound of the formula:

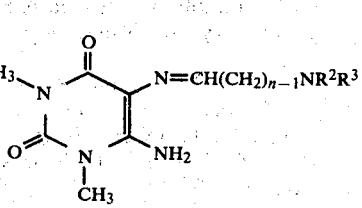

(wherein $R^2$, $R^3$ and n are as defined hereinbefore) which is then reduced to give the desired compound of formula VI.

The reduction may be effected by conventional techniques.

The acid addition salts of the compounds of formula I may be prepared by reaction with the appropriate acid to give the desired addition salt. The acid addition salts may be re-converted to free compounds of formula I by reaction with one molar proportion of a base.

This invention naturally extends to the compounds of formula I and the acid addition salts thereof whenever prepared by a process as described hereinbefore.

The compounds of the invention are highly active in decreasing heart rate and blood pressure while increasing coronary blood flow in animals, including man. They may thus be of use in the treatment of cardiac disorders, for example congestive heart failure, angina pectoris, or hypertension.

The dosage administered will, naturally, vary with the compound employed, the mode of administration and the treatment desired. However, in general, satisfactory results are obtained when the compounds are administered at a dosage of from 0.1 to 60 mg per kilogram of animal body weight per day. For man, the indicated total daily dosage is in the range of from about 1 mg to 1,500 mg. which may be administered in divided doses, for example 2 or 3 times a day, or in sustained release form. Thus unit dose forms suitable for administration comprise from about 0.3 mg to 200 mg of the compound.

The compounds may be administered in admixture with a pharmaceutically acceptable adjuvant, diluent or carrier, the composition used depending on many factors including the disorder to be treated. The compounds may be administered parenterally, orally or by inhalation.

In another aspect the invention provides a method of increasing heart blood flow in an animal, either human or non-human, which method comprises administering to the animal an effective amount of one or more compounds of the invention.

The following Examples are now given, though only by way of illustration of the invention. All temperatures quoted are in °C.

EXAMPLE 1

8-Methyl-7-(2-N,N-diethylaminoethyl)theophylline hydrochloride

Sodium hydride (1.25 g, 0.052 M) was washed free of oil by dry petroleum ether and was suspended in dry dimethylformamide (250 ml) in an atmosphere of nitrogen. 8-Methyltheophylline was added with stirring which was continued until all evolution of hydrogen had ceased. 2-Diethylaminoethylchloride hydrochloride (4.42 g, 0.026 M) was then added and the mixture was stirred for 3 hours under nitrogen. The reaction was quenched by addition of water (300 ml) and the mixture was extracted with ethyl acetate. The organic layer was washed with water, dried over magnesium sulphate, filtered and evaporated to dryness leaving an oil. This was dissolved in ethanol (150 ml) to which solution was then added saturated ethanolic hydrogen chloride (50 ml). The resulting solution was evaporated to dryness and the resulting solid was crystallised from isopropanol to give the title compound as white needles 3.7 g (44%) m.p. 229°–232°.
Analysis:
Found: C, 51.1, H, 7.6, N 21.5, Cl 10.8%, $C_{14}H_{23}N_5O_2.HCl$ Requires: C, 51.0, H, 7.3, N 21.25, Cl 10.8%.

EXAMPLES 2–5

By the process of Example 1, using the appropriate N,N-dialkylaminoalkyl chloride hydrochloride on 8-methyltheophylline or 8-ethyltheophylline, the following compounds were prepared:

2. 8-methyl-7-(2-N,N-dimethylaminoethyl)theophylline hydrochloride, mp 285°–6° C.
3. 8-methyl-7-/2-N,N-di(1-methylethyl)aminoethyl/-theophylline hydrochloride, mp 262°–3° C.
4. 8-ethyl-7-(2-N,N-dimethylaminoethyl)theophylline hydrochloride, mp 275°–6° C.
5. 8-ethyl-7-(2-N,N-diethylaminoethyl)theophylline hydrochloride, mp 264°–7° C.

EXAMPLE 6

8-Ethyl-7-(3-N,N-di-n-butylaminopropyl)theophylline (a) 8-Ethyl-7-(3-phenoxypropyl)theophylline A suspension of 8-ethyltheophylline (20.8 g; 0.1 M) in dry dimethylformamide (100 ml) was added to an oil free suspension of sodium hydride (2.4 g; 0.1 M) in dry dimethylformamide (100 ml) and the mixture was stirred for 30 minutes. 3-Phenoxypropylbromide (21.5 g; 0.1 M) was added and the mixture was stirred at room temperature for 24 hours. The resulting suspension was poured into water and the precipitate was filtered off and dried. The solid was crystallised from ethanol to give 8-ethyl-7-(3-phenoxy propyl)theophylline as white prisms 23.6 g (69%) mp 107°–8°.
Analysis:
Found: C, 62.6; H, 6.8; N, 15.8%, $C_{18}H_{22}N_4O_3$ requires with 0.8% $H_2O$, C, 62.6; H, 6.5; N, 16.2%.

(b) 7-(3-Bromopropyl)-8-ethyltheophylline

A mixture of 8-ethyl-7-(3-phenoxypropyl)theophylline (23.0 g; 0.067 M) and 48% aqueous hydrogen bromide (150 ml) was heated at reflux for 20 hours. The mixture was cooled and poured into dilute aqueous sodium hydroxide solution. The suspension was extracted with chloroform and the organic phase was washed with water, aqueous 10% sodium hydroxide solution and water and was dried ($MgSO_4$), filtered and the filtrate was evaporated to dryness leaving a colourless solid. This solid was crystallised from ethanol to give the required compound as colourless prisms, (8.2 g) (82%) mp 119°–120°.
Analysis:
Found: C, 43.08; H, 5.6; N, 16.4; Br, 23.1%, $C_{12}H_{17}BrN_4O_2$ requires with 1.4% $H_2O$, C, 43.1; H, 5.3; N, 16.7; Br, 23.8%, (c) 8-Ethyl-7-(3-N,N-di-n-butylaminopropyl)theophylline hydrochloride A solution of 7-(3-bromopropyl)-8-ethyl theophylline (6.58; 0.02 M) and di-n-butylamine (5.16 g; 0.04 M) in dry toluene (100 ml) was heated under reflux for 20 hours. The mixture was cooled and filtered, and the filtrate was evaporated to dryness leaving a yellow oil (7.2 g, 95%). This oil was treated with 1 N HCl (19 ml; 0.019 M) and the resulting solution was evaporated to dryness leaving a solid which was crystallised from propan-2-ol to afford the title compound as colourless prisms. 6.0 g (72%) mp 181°–2°.
Analysis:
Found: C, 58.1; H, 8.8; N, 16.8; Cl, 8.7%, $C_{20}H_{35}N_5O_2.HCl$ requires: C, 57.9; H, 8.7; N, 16.9; Cl, 8.5%.

EXAMPLES 7–32

By processes analogous to that of Example 6 employing the appropriate 8-alkyl-theophylline as starting material, the following compounds were prepared:

7. 8-methyl-7-(3-N,N-dimethylaminopropyl)theophylline hydrochloride, mp 300° C.
8. 8-methyl-7-(4-N,N-dimethylaminobutyl)theophylline hydrochloride, mp 60° C. (d).
9. 8-ethyl-7-(3-N,N-dimethylaminopropyl)theophylline hydrochloride, mp 240°–1° C.

10. 8-ethyl-7-(4-N,N-dimethylaminobutyl)theophylline hydrochloride, mp 196°-7° C.
11. 8-methyl-7-(3-N,N-diethylaminopropyl)theophylline hydrochloride, mp 212°-3° C.
12. 8-methyl-7-(4,N,N-diethylaminobutyl)theophylline hydrochloride, mp 221°-3° C.
13. 8-ethyl-7-(3-N,N-diethylaminopropyl)theophylline hydrochloride, mp 241°-2° C.
14. 8-(1-phenylethyl)-7-(2-N,N-diethylaminoethyl)-theophylline hydrochloride, mp 225°-9° C.
15. 8-methyl-7-(2-N,N-dipropylaminoethyl)theophylline hydrochloride, mp 222°-5° C.
16. 8-methyl-7-(3-N,N-dipropylaminopropyl)theophylline hydrochloride, mp 218°-220° C.
17. 8-methyl-7-(4-N,N-dipropylaminobutyl)theophylline hydrochloride, mp 201°-2° C.
18. 8-ethyl-7-(3-N,N-dipropylaminopropyl)theophylline hydrochloride, mp 221°-2° C.
19. 8-ethyl-7-(4-N,N-dipropylaminobutyl)theophylline hydriodide, mp 219°-220° C.
20. 8-methyl-7-(3-N,N-di-isopropylaminopropyl)-theophylline hydrochloride, mp 239°-241° C.
21. 8-ethyl-7-(3-N,N-di-isopropylaminopropyl)theophylline hydrochloride, mp 231°-2° C.
22. 8-ethyl-7-(4-N,N-di-isopropylaminobutyl)theophylline hydriodide, mp 184°-5° C.
23. 8-methyl-7-(2-N,N-dibutylaminoethyl)theophylline hydrochloride, mp 167°-8° C.
24. 8-methyl-7-(3-N,N-dibutylaminopropyl)theophylline hydrochloride, mp 133°-4° C.
25. 8-methyl-7-(4-N,N-dibutylaminobutyl)theophylline hydrochloride, mp 142°-5° C.
26. 8-ethyl-7-(4-N,N-dibutylaminobutyl)theophylline hydriodide, mp 149°-150° C.
27. 8-(4-chlorophenyl)-7-(2-N,N-diethylaminoethyl)-theophylline hydrochloride, mp 284°-289° C.
28. 8-phenyl-7-(2-N,N-diethylaminoethyl)theophylline hydrochloride, mp 260°-262° C.
29. 8-(4-methylphenyl)-7-(2-N,N-diethylaminoethyl)-theophylline hydrochloride, mp 265°-266° C.
30. 8-(4-methoxyphenyl)-7-(2-N,N-diethylaminoethyl)theophylline hydrochloride, mp 250° C.
31. 8-(3,4-dichlorophenyl)-7-(2-N,N-diethylaminoethyl)theophylline hydrochloride, mp 253°-258° C.
32. 8-trifluoromethyl-7-(2-N,N-diethylaminoethyl)-theophylline hydrochloride, mp 231°-232° C.
33. 8-methyl-7-[2-(1-piperidino)ethyl]theophylline hydrochloride.
34. 8-methyl-7-[2-(N-methyl-N-benzylamino)ethyl]-theophylline hydrochloride.
35. 8-methyl-7-[2-N,N-di(2-phenyethyl)aminoethyl]-theophylline hydrochloride.
36. 8-n-pentyl-7-(2-N,N-diethylaminoethyl)theophylline hydrochloride.

EXAMPLE 37

8-Methyl-7-(2-diethylaminoethyl)theophylline

A solution of 7-(2-diethylaminoethyl)theophylline (2.79 g) in dry tetrahydrofuran (50 ml) under nitrogen was cooled to −15° C. and butyl lithium (10 ml of 1 M solution in tetrahydrofuran) was added by syringe. The mixture was stirred for 30 minutes, then methyl iodide (1.42 g) was added, the mixture was stirred, and was allowed to warm to room temperature. After 3 hours, water was added and the mixture was extracted with chloroform. The chloroform extracts were washed with water, dried, filtered and evaporated to dryness. The residual oil was then taken up in ethanol (20 ml) and treated with ethanolic hydrogen chloride. The solution was then evaporated to dryness and the residue was crystallised from isopropyl alcohol to give 8-methyl-7-(2-diethylaminoethyl)theophylline hydrochloride (1.6 g), mp 230°-232° C.

EXAMPLE 38

8-Ethyl-7-(2-diethylaminoethyl)theophylline

The procedure of Example 37 was followed up to the addition of the methyl iodide. Thereafter the mixture was stirred for 3 hours, then cooled to −15° C. 1 Equivalent of butyl lithium (10 ml) was added, the solution was stirred for 30 minutes, a further portion of methyl iodide (1.42 g) was added and the solution was allowed to warm to room temperature. It was then stirred for 3 hours and worked up as in Example 37 to give 8-ethyl-7-(2-diethylaminoethyl)theophylline hydrochloride (1.7 g), mp 260°-263° C.

EXAMPLE 39

8-Methyl-7-(2-diethylaminoethyl)theophylline

A mixture of acetic anhydride (50 ml) and 4,5-diamino-1,3-dimethylpyrimidine-2,6-dione (5.4 g) was heated at reflux for 30 minutes. The mixture was then cooled, and the crystalline matter which separated was filtered off to give 5-acetylamino-4-amino-1,3-dimethylpyrimidine-2,6-dione as white needles. A suspension of oil-free sodium hydride (1.3 g) in dry dimethylformamide (5.0 ml) was stirred under nitrogen at 0° C. while the acetylamino compound was added. The mixture was then stirred for 30 minutes. Diethylaminoethyl chloride hydrochloride (4.64 g) was added, then the mixture was warmed to room temperature and stirred for 3 hours. Water was added, and the mixture was extracted with chloroform. The organic extracts were washed with water, dried and filtered, and the filtrate was evaporated to dryness. The solid residue was treated with 2 N aqueous sodium hydroxide (50 ml) at 100° C. for 30 minutes, then the mixture was extracted with chloroform, dried, filtered and evaporated to dryness. The oil product was dissolved in ethanol, treated with ethanolic hydrogen chloride and evaporated to dryness. The residue was recrystallised from isopropyl alcohol to give 8-methyl-7-(2-diethylaminoethyl)theophylline hydrochloride (3.1 g), mp 230°-232° C.

EXAMPLE 40

8-Methyl-7-(2-diethylaminoethyl)theophylline

Xanthine (30.4 g) was dissolved in aqueous sodium hydroxide solution (8 g in 500 ml) containing ethanol (100 ml). The solution was stirred, and diethylaminoethyl chloride (liberated from its salts) (27.0 g) was added at room temperature. The mixture was stirred on a steam bath for 18 hours, then evaporated to dryness. The residue was fractionally recrystallised from isopropyl alcohol to give 7-(2-diethylaminoethyl)xanthine (7.5 g). The solid was stirred in dry tetrahydrofuran (1 liter) at −15° C. under nitrogen. Butyl lithium (90 ml) was then added by syringe, and the mixture was stirred for 2 hours. Methyl iodide (12.8 g) was then added and the mixture was stirred and allowed to warm to room temperature. It was then stirred overnight, quenched with water and extracted with chloroform. The extracts were then washed, dried, filtered, and the filtrate was evaporated to dryness. The residue was dissolved in ethanol and treated with ethanolic hydrogen chloride, then evaporated to dryness. The residue was recrystallised from isopropyl alcohol to give 8-methyl-7-(2-diethylaminoethyl)theophylline hydrochloride (3.1 g), mp 230°–232° C.

We claim:
1. The substituted theophyllines of the formula:

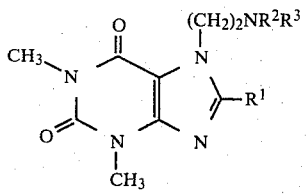

wherein $R^1$, $R^2$ and $R^3$, which may be the same or different, each represent alkyl of 1 to 6 carbon atoms, cycloalkyl of 3 to 7 carbon atoms, or phenyl each of which may be unsubstituted or substituted by one or more hydroxy groups, alkoxy or alkylthio groups of 1 to 4 carbon atoms, halogen atoms, cyano groups, nitro groups, carboxy groups, alkoxycarbonyl groups of 2 to 5 carbon atoms, amino groups, alkylamino groups of 1 to 4 carbon atoms or dialkylamino groups of 2 to 8 carbon atoms, or when the group is phenyl, by one or more alkyl groups of 1 to 4 carbon atoms;
or $R^2$ and $R^3$ together represent a hydrocarbon chain or 3 to 6 carbon atoms optionally interrupted by a heteroatom;
and n represents an integer of from 1 to 6,
and the acid addition salts thereof.

2. A compound according to claim 1 wherein $R^1$, $R^2$ and $R^3$ each represent alkyl of 1 to 4 carbon atoms, cycloalkyl of 5 or 6 carbon atoms, or phenyl, each of which is unsubstituted or substituted by one or more hydroxy, methoxy, ethoxy, methylthio, ethylthio, cyano, nitro, carboxy, methoxycarbonyl, ethoxycarbonyl, amino, methylamino or dimethylamino groups, or by one or more fluorine, chlorine or bromine atoms, or when the group is phenyl, by one or more methyl or ethyl groups.

3. A compound according to claim 1 or claim 2 wherein $R^1$ represents an unsubstituted methyl, ethyl, n-propyl, isopropyl, n-butyl or t-butyl group.

4. A compound according to claim 1 wherein $R^2$ and $R^3$ are identical.

5. A compound according to claim 1 wherein $R^2$ and $R^3$ each represent methyl, ethyl, n-propyl, isopropyl, n-butyl or t-butyl.

6. A compound according to claim 1 which is:
8-methyl-7-(2-N,N-diethylaminoethyl)theophylline;
8-methyl-7-(2-N,N-dimethylaminoethyl)theophylline;
8-methyl-7-(2-N,N-di-isopropylaminoethyl)theophylline;
8-ethyl-7-(2-N,N-dimethylaminoethyl)theophylline;
8-ethyl-7-(2-N,N-diethylaminoethyl)theophylline;
8-ethyl-7-(3-N,N-di-n-butylaminopropyl)theophylline;
8-methyl-7-(3-N,N-dimethylaminopropyl)theophylline;
8-methyl-7-(4-N,N-dimethylaminobutyl)theophylline;
8-ethyl-7-(3-N,N-dimethylaminopropyl)theophylline;
8-ethyl-7-(4-N,N-dimethylaminobutyl)theophylline;
8-methyl-7-(3-N,N-diethylaminopropyl)theophylline;
8-methyl-7-(4,N,N-diethylaminobutyl)theophylline;
8-ethyl-7-(3-N,N-diethylaminopropyl)theophylline;
8-methyl-7-(2-N,N-dipropylaminoethyl)theophylline;
8-methyl-7-(3-N,N-dipropylaminopropyl)theophylline;
8-methyl-7-(4-N,N-dipropylaminobutyl)theophylline;
8-ethyl-7-(3-N,N-dipropylaminopropyl)theophylline;
8-ethyl-7-(4-N,N-dipropylaminobutyl)theophylline;
8-methyl-7-(3-N,N-di-isopropylaminopropyl)theophylline;
8-ethyl-7-(3-N,N-di-isopropylaminopropyl)theophylline;
8-ethyl-7-(4-N,N-di-isopropylaminobutyl)theophylline;
8-methyl-7-(3-N,N-dibutylaminopropyl)theophylline;
8-methyl-7-(4-N,N-dibutylaminobutyl)theophylline;
8-ethyl-7-(4-N,N-dibutylaminobutyl)theophylline;
8-(4-chlorophenyl)-7-(2-N,N-diethylaminoethyl)-theophylline;
8-phenyl-7-(2-N,N-diethylaminoethyl)theophylline;
8-(4-methylphenyl)-7-(2-N,N-diethylaminoethyl)-theophylline;
8-(4-methoxyphenyl)-7-(2-N,N-diethylaminoethyl)-theophylline;
8-(3,4-dichlorophenyl)-7-(2-N,N-diethylaminoethyl)-theophylline;
8-trifluoromethyl-7-(2-N,N-diethylaminoethyl)-theophylline;
8-methyl-7-[2-(1-piperidino)ethyl]theophylline;
8-n-pentyl-7-(2-N,N-diethylaminoethyl)theophylline;
or an acid addition salt thereof.

7. A compound according to claim 1 in the form of an acid addition salt formed with hydriodic, hydrochloric, hydrobromic, sulphuric, nitric, citric, tartaric or p-toluenesulphonic acid.

8. A pharmaceutical composition useful in the treatment of cardiac disorders which comprises an effective amount of one or more substituted theophyllines according to claim 1, in association with a suitable pharmaceutically acceptable adjuvant, diluent or carrier.

* * * * *